(12) United States Patent
McAdams et al.

(10) Patent No.: US 7,897,832 B2
(45) Date of Patent: *Mar. 1, 2011

(54) COMPOSITIONS, ASSEMBLIES, AND METHODS APPLIED DURING OR AFTER A DENTAL PROCEDURE TO AMELIORATE FLUID LOSS AND/OR PROMOTE HEALING, USING A HYDROPHILIC POLYMER SPONGE STRUCTURE SUCH AS CHITOSAN

(75) Inventors: Staci Ann McAdams, Milwaukie, OR (US); William David Block, Lake Oswego, OR (US); Simon John McCarthy, Portland, OR (US); Kenton W. Gregory, Portland, OR (US)

(73) Assignee: HemCon Medical Technologies, Inc., Portland, OR (US)

( * ) Notice: Subject to any disclaimer, the term of this patent is extended or adjusted under 35 U.S.C. 154(b) by 1049 days.

This patent is subject to a terminal disclaimer.

(21) Appl. No.: 11/261,351

(22) Filed: Oct. 28, 2005

(65) Prior Publication Data

US 2006/0089584 A1    Apr. 27, 2006

Related U.S. Application Data

(63) Continuation-in-part of application No. 10/743,052, filed on Dec. 23, 2003, now Pat. No. 7,371,403, which is a continuation-in-part of application No. 10/480,827, filed as application No. PCT/US02/18757 on Jun. 14, 2002, now Pat. No. 7,482,503.

(60) Provisional application No. 60/298,773, filed on Jun. 14, 2001.

(51) Int. Cl.
A61F 15/00 (2006.01)
A61C 5/14 (2006.01)

(52) U.S. Cl. .......................... 602/48; 433/136
(58) Field of Classification Search ........................ None
See application file for complete search history.

(56) References Cited

U.S. PATENT DOCUMENTS

| | | | |
|---|---|---|---|
| 2,610,625 A | 9/1952 | Sifferd et al. | |
| 3,551,556 A | 12/1970 | Kliment et al. | |
| 3,801,675 A | 4/1974 | Russell | |
| 3,849,238 A | 11/1974 | Gould et al. | |
| 3,902,497 A | 9/1975 | Casey | |
| 4,394,373 A | 7/1983 | Malette et al. | |
| 4,452,785 A | 6/1984 | Malette et al. | |
| 4,460,642 A | 7/1984 | Errede et al. | |
| 4,501,835 A | 2/1985 | Berke | |
| 4,532,134 A | 7/1985 | Malette et al. | |
| 4,541,426 A | 9/1985 | Webster | |
| 4,952,618 A | 8/1990 | Olsen | |
| 4,973,493 A * | 11/1990 | Guire | 427/2.24 |
| 4,977,892 A | 12/1990 | Ewall | |
| 5,006,071 A | 4/1991 | Carter | |
| 5,454,719 A | 10/1995 | Hamblen | |
| 5,700,476 A | 12/1997 | Rosenthal et al. | |
| 5,836,970 A | 11/1998 | Pandit | |
| 5,858,350 A | 1/1999 | Vournakis et al. | |
| 6,103,369 A | 8/2000 | Lucast et al. | |
| 6,448,462 B2 | 9/2002 | Groitzsch et al. | |
| 6,566,577 B1 | 5/2003 | Addison et al. | |
| 6,693,180 B2 | 2/2004 | Lee et al. | |
| 7,371,403 B2 * | 5/2008 | McCarthy et al. | 424/445 |
| 2002/0071855 A1 | 6/2002 | Sadozai et al. | |
| 2004/0243043 A1 | 12/2004 | McCarthy et al. | |
| 2005/0036955 A1 | 2/2005 | DeGould | |
| 2005/0038369 A1 | 2/2005 | Gregory et al. | |
| 2005/0123581 A1 | 6/2005 | Ringeisen et al. | |
| 2005/0137512 A1 | 6/2005 | Campbell et al. | |
| 2005/0147656 A1 | 7/2005 | McCarthy et al. | |
| 2006/0089584 A1 * | 4/2006 | McAdams et al. | 602/48 |

FOREIGN PATENT DOCUMENTS

| | | | |
|---|---|---|---|
| EP | 0643963 A2 * | 4/1994 | |
| JP | 60-142927 | 7/1985 | |
| JP | 60-090507 | 4/1988 | |
| WO | WO 03/079946 | 10/2003 | |

OTHER PUBLICATIONS

Fwu-Long Mi et al., "*Fabrication and characterization of a sponge-like asymmetric chitosan membrane as a wound dressing.*" Biomaterials 22 pp. 165-173 (2001), Elsevier Science Ltd., London and New York.
Michele W. Chan et al., "*Comparison of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage.*" The Journal of Trauma 48(3) pp. 454-458 (2000) Lippincott Williams & Wilkins, Inc. U.S.A.
David J. Cole et al., "*A pilot study evaluating the efficacy of a fully acetylated ply-N-acetyl glucosamine membrane formulation as a topical hemostatic agent,*"Surgery 126(3) pp. 510-517 (1999) Mosby, Inc. U.S.A.
Paul A. Sanford et al., "*Biomedical Applicants of High-Purity Chitosan,*" ACS Symposium Series 467 pp. 430-445 (1991) American Chemical Society, Washington D.C.
William G. Malette et al., "*Chitosan: A New Hemostatic,*"The Annals of Thoracic Surgery 36(1) pp. 55-58 (1983).
Roger Olsen et al., "*Biomedical Applicants of Chitin and its Derivatives,*" Chitin and Chitosan pp. 813-829 (1988) Elsevier Applied Science, London and New York.

* cited by examiner

*Primary Examiner*—Shanon A Foley
(74) *Attorney, Agent, or Firm*—Miller Nash LLP (57) ABSTRACT

Dental dressing assemblies are formed from hydrophilic polymer sponge structures, such as a densified chitosan biomaterial.

6 Claims, 5 Drawing Sheets

COMPOSITIONS, ASSEMBLIES, AND METHODS APPLIED DURING OR AFTER A DENTAL PROCEDURE TO AMELIORATE FLUID LOSS AND/OR PROMOTE HEALING, USING A HYDROPHILIC POLYMER SPONGE STRUCTURE SUCH AS CHITOSAN

RELATED APPLICATIONS

This application is a continuation-in-part of U.S. patent application Ser. No. 10/743,052, filed on Dec. 23, 2003, now U.S. Pat. No. 7,371,403 entitled "Wound Dressing and Method of Controlling Severe Life-Threatening Bleeding,", which is a continuation-in-part of U.S. patent application Ser. No. 10/480,827, filed on Oct. 6, 2004, now U.S. Pat. No. 7,482,503 entitled "Wound Dressing and Method of Controlling Severe Life-Threatening Bleeding," which was a national stage filing under 37 C.F.R. §371 of International Application No. PCT/US02/18757, filed on Jun. 14, 2002, which claims the benefit of provisional patent application Ser. No. 60/298,773 filed Jun. 14, 2001, which are each incorporated herein by reference.

FIELD OF THE INVENTION

The invention is generally directed to compositions, assemblies, and methods applied during or after a dental procedure to ameliorate bleeding, fluid seepage or weeping, or other forms of fluid loss, as well as promote healing.

BACKGROUND OF THE INVENTION

Figures 1, 2, 3A, 3B:
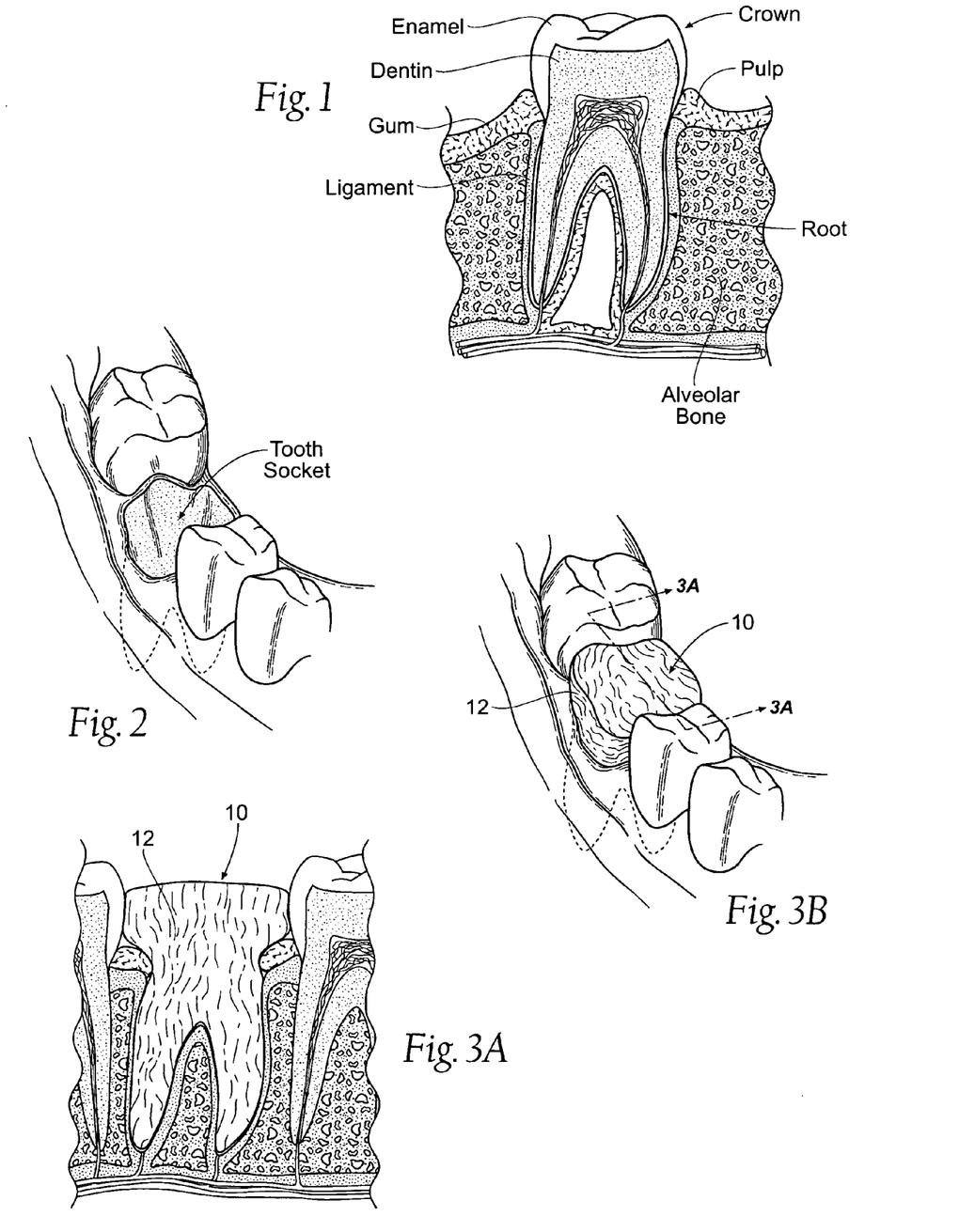
FIG. 1 is an anatomic view of a healthy tooth.
FIG. 2 is an anatomic view of a tooth extraction site in an oral cavity, showing a tooth socket left open by extraction of the tooth.
FIGS. 3A and 3B are, respectively, an anatomic lateral perspective view and an anatomic lateral section view of a tooth extraction site into which a dental pad assembly has been placed, the dental pad assembly being capable of adhering to body tissue in the presence of blood, fluid, or moisture to stanch, seal, or stabilize the extraction site during the healing process.

FIG. 1 is an anatomic view of a healthy tooth. The tooth includes a crown and a root. The root is encased by a supporting ligament in alveolar (jaw) bone. The ligament comprises a tough band of shock-absorbing connective tissue, which physically binds the tooth root to the jaw bone. The hole occupied by the tooth in the bone is called the tooth socket.

The crown of the tooth is exposed above the gum. A hard shiny outer surface, called the enamel, covers the crown. Below the enamel is dentin, which is microscopically porous hard tissue. At the center of the tooth is the pulp chamber, which houses the pulp consisting of blood vessels and nerve tissues.

A tooth may become damaged, or decayed, e.g., due to erosion of the calcium in the tooth's enamel by bacteria. This, in turn, can lead to erosion of the dentin beneath the enamel. As the decay continues, bacteria can migrate through the porous dentin and infect the pulp. An immune response to the infection can follow, causing the blood vessels around the tooth to enlarge and press against the nerves entering the tooth. The result is tooth ache.

There are various dental procedures for intervening when these or other conditions affecting the oral cavity and its anatomic structures arise. These procedures are routinely performed by general practitioners, dentists, oral surgeons, maxillofacial surgeons, and peridontistics.

For example, endodontic surgery, also called root canal therapy, can, under many circumstances, intervene to remove the bacteria, nerve tissue, organic debris, and bacterial toxins from within the inner aspects of a decaying tooth. Following this, the practitioner fills in and seals off the interior of the tooth. Currently, there are about 16 million root canals performed annually.

If the decay has progressed too far, removal or extraction of the tooth may be indicated. Currently, there are more than 30 million extractions performed each year. During a simple extraction, a dentist will grasp the tooth with a tool, e.g., forceps, and rock the tooth back and forth. This rocking motion loosens the tooth from the alveolar bone by breaking the ligaments that hold the tooth in place. The tooth is then pulled from the socket, leaving the tooth socket open.

Removal or extraction of the tooth may also be indicated when the presence of the tooth is causing crowding, or malocclusion, or preventing another tooth (e.g., a wisdom tooth) from erupting, or in preparation for orthodontic treatment ("braces"). A tooth extraction may also be indicated because of advanced periodontal (gum) disease. Sometimes, if the tooth selected for extraction is not fully erupted above the gum, it may be necessary to first remove some of the overlying gum and bone tissue in order to access the tooth for extraction.

During and after such conventional dental procedures—e.g., endodontic surgery, or periodontal surgery, orthodontic treatment, tooth extractions, orthognathic surgery, biopsies, and other oral surgery procedures—bleeding, fluid seepage or weeping, or other forms of fluid loss typically occur. Bleeding, fluid seepage or weeping, or other forms of fluid loss can also occur in the oral cavity as a result of injury or trauma to tissue and structures in the oral cavity. In this regard, there are about two million teeth lost each year due to accidents. Swelling and residual bleeding can be typically expected to persist during the healing period following the procedure or injury. During the healing period, new gum tissue will grown into the gap left by the extraction.

It is thereby desirable during the healing period to take steps to stanch, seal, and/or stabilize the site of surgical intervention—or the site of tissue injury or trauma—against fluid loss due to bleeding, fluid seepage or weeping. During and after dental procedures or injury to the oral cavity, there is a need for quick and effective hemostasis.

For example, following a tooth extraction, the quick cessation of bleeding and the formation of a blood clot on the wound in the open tooth socket are very desirable. Indeed, during the entire healing period following an extraction—which can take from one to two weeks—it is important to preserve conditions conducive to hemostasis, so that the blood clot that forms within the socket does not break down and/or dislodge. If the clot breaks down and/or dislodges, a condition known as a dry socket (also called alveolar osteitis) results. Dry socket conditions can also occur for the same reason during the treatment of cystic cavity defects in the jaw. Dry socket can cause pain and discomfort, which will subside only as the socket heals through a secondary healing process.

Conventionally, cotton packs and rolled or folded gauze pads are commonly used to stem the bleeding precipitated during and after dental procedures. While the presence of such materials may absorb blood and fluids, they do not promote or create conditions conducive to rapid and long term hemostasis or healing. There still remains a need for improved hemostatic compositions, assemblies, and methods that can be applied during or after dental procedures.

SUMMARY OF THE INVENTION

The invention provides assemblies, systems and methods for treating tissue or bone in an oral cavity or an adjacent anatomic structure, comprising the placement of a hydrophilic polymer sponge structure.

One aspect of the invention provides a hydrophilic polymer sponge structure that is shaped, sized, and configured for placement in association with tissue or bone in an oral cavity or an adjacent anatomic structure, as well as a method for placing the hydrophilic polymer sponge structure in association with the tissue or bone in the oral cavity or the adjacent anatomic structure.

Another aspect of the invention includes systems and methods for performing a dental surgical procedure, which can comprise, e.g., a tooth extraction; or endodontic surgery; or periodontal surgery; or orthodontic treatment; or orthognathic surgery; or a biopsy; or gingival surgery; or osseous surgery; or scaling or root planning; or periodontal maintenance; or complete maxillary or mandibular denture; or complete or partial denture adjustment; or denture rebase or reline; or soft tissue surgical extraction; or bony surgical extraction; or installation of an occlusal orthotic device or occlusal guard or occlusal adjustment; or oral surgery involving jaw repair; treatment of cystic cavity defects in the jaw; or new bone growth or bone growth promotion; or any other surgical procedure or intervention affecting tissue in the oral cavity, anatomic structures in the oral cavity, or alveolar (jaw) bone. According to this aspect of the invention, the systems and methods place a hydrophilic polymer sponge structure in association with tissue or bone affected by the surgical procedure.

Another aspect of the invention provides systems and methods for treating tissue in the oral cavity or alveolar (jaw) bone as a result of an accident that causes injury or trauma to the tissue or bone. According to this aspect of the invention, the systems and methods place a hydrophilic polymer sponge structure in association with the treated tissue or bone.

The assemblies, systems and methods that make use of the hydrophilic polymer sponge structure stanch, seal, or stabilize a site of tissue or bone injury, tissue or bone trauma, or tissue or bone surgery. The use of hydrophilic polymer sponge structure can also form an anti-microbial or anti-viral barrier; and/or promote coagulation; and/or release a therapeutic agent; and/or treat a periodontal or bone surface; and/or combinations thereof.

In accordance with all aspects of the invention, the hydrophilic polymer sponge structure desirably includes a chitosan biomaterial which has been densified by compression prior to use to a density of between 0.6 to 0.1 g/cm3.

Other features and advantages of the invention shall be apparent based upon the accompanying description, drawings, and claims.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. The Dental Pad Assembly

FIG. 2 shows a tooth socket that has been left open following a tooth extraction. FIGS. 3A and 3B show a dental pad assembly 10 that embodies features of the invention, after placement into the open tooth socket of the extraction site. In FIGS. 3A and 3B, the dental pad assembly 10 has been shaped, sized, and configured to be capable of insertion or "packing" into an open tooth socket following extraction of the tooth. The extraction can involve a single tooth (as shown) or multiple teeth.

The dental pad assembly 10 comprises a tissue dressing matrix 12. The tissue dressing matrix 12 includes a biocompatible material that reacts in the presence of blood, body fluid, or moisture to become a strong adhesive or glue. Desirably, the tissue dressing matrix also possesses other beneficial attributes, for example, anti-bacterial and/or anti-microbial and/or anti-viral characteristics, and/or characteristics that accelerate or otherwise enhance coagulation and the body's defensive reaction to injury.

The tissue dressing matrix 12 desirably comprises a hydrophilic polymer form, such as a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase.

In a preferred embodiment, the biocompatible material of the matrix 12 comprises a non-mammalian material, which is most preferably poly [β-(1→4)-2-amino-2-deoxy-D-glucopyranose, which is more commonly referred to as chitosan.

Due to the special properties of the chitosan matrix 12, the dental pad assembly 10 is capable of adhering to tissue within the socket in the presence of blood, or body fluids, or moisture. The presence of the dental pad assembly 10 stanches, seals, and/or stabilizes the extraction site, while establishing conditions conducive to the formation and maintenance of a blood clot at the wound during the healing process.

Figures 4A, 4B, 5A, 5B:
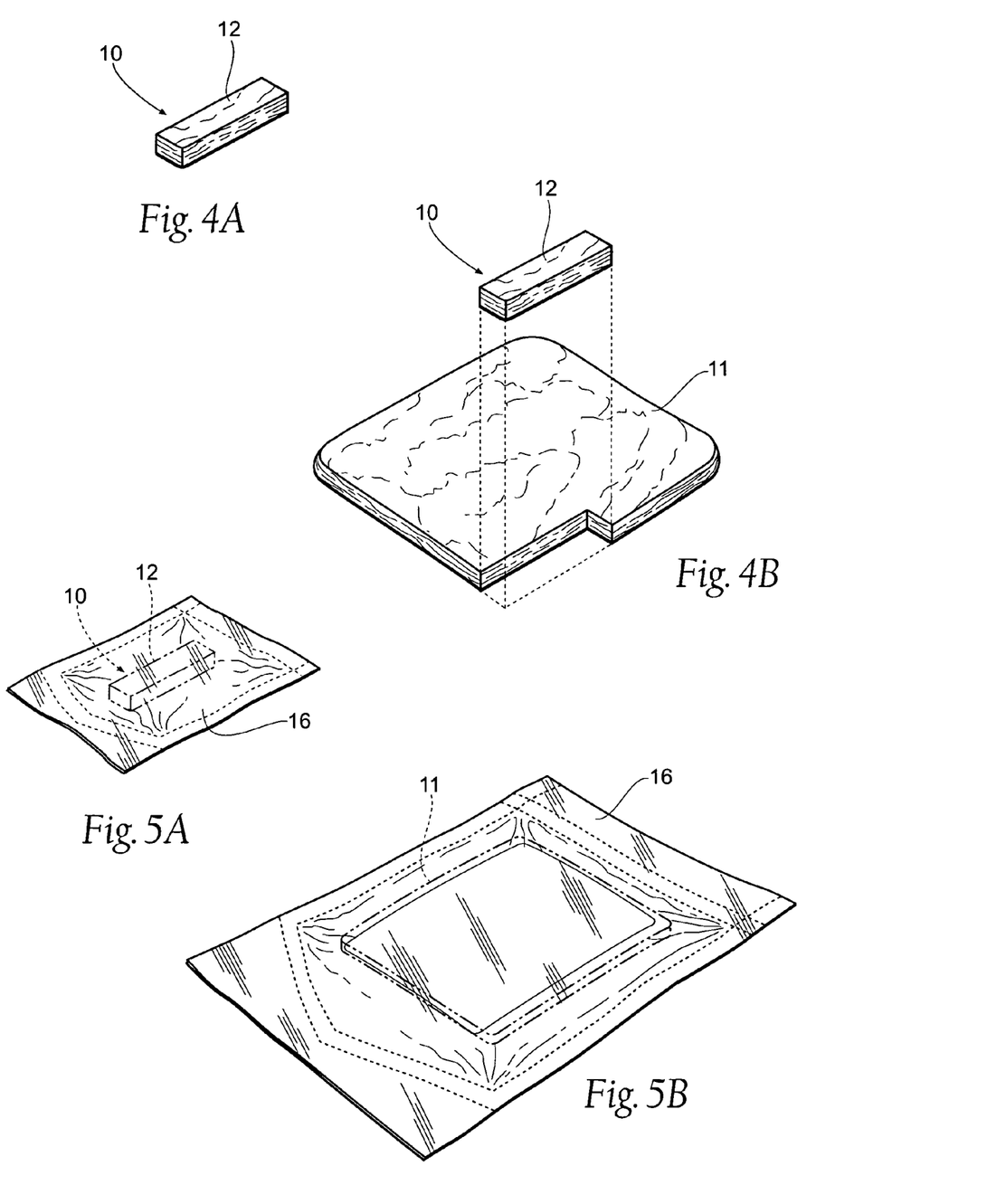
FIG. 4A is a perspective view of the dental pad assembly shown in FIGS. 3A and 3B prior to being finally shaped and configured for placement within the extraction site.
FIG. 4B is a perspective view of the dental pad assembly shown in FIG. 4A cut to a desired size from a larger source pad assembly, prior to being finally shaped and configured for placement within the tooth extraction site.
FIGS. 5A and 5B are, respectively, the dental pad assembly shown in FIG. 4A and the source pad assembly shown in FIG. 4B packaged in a sterilized condition within a sealed pouch for use.

FIG. 4A shows a representative dental pad assembly 10 in its condition prior to use. The size, shape, and configuration of the dental packing pad assembly 10 can vary according to its intended use, which includes taking into account the topology and morphology of the site to be treated and the age/status of the patient (e.g., adult or child). The pad assembly 10 can be rectilinear, elongated, square, round, oval, or a composite or complex combination thereof. Desirably, the shape, size, and configuration of pad assembly 10 can be specially formed and adapted to the topology and morphology of the site of application, by cutting, bending, or molding, either during use or in advance of use. FIG. 4B shows that one or more dental pad assemblies 10 of the same or different desired shapes, sizes, and configurations can be cut from a larger source pad assembly 11.

FIGS. 3A and 3B show the application of the pad assembly 10 within an open tooth socket following an extraction. It should be appreciated that the pad assembly 10 can be shaped, sized, and configured in various ways depending upon the topology and morphology of the tissue site intended to be treated in the oral cavity or surrounding anatomic structures. The targeted treatment site treated can comprise tissue cut or altered or otherwise affected during a dental surgical procedure, e.g., during a tooth extraction. Still, the pad assembly 10 can be shaped, sized, and configured for other types of dental surgical procedures, e.g., endodontic surgery, or periodontal surgery, or orthodontic treatment, or orthognathic surgery, or biopsy, or gingival surgery, osseous surgery, or scaling or root planning, or periodontal maintenance, or complete maxillary or mandibular denture, or complete or partial denture adjustment, or denture rebase or reline, or soft tissue surgical extraction, or bony surgical extraction, or installation of an occlusal orthotic device or occlusal guard or occlusal adjustment, or oral surgery involving jaw repair, or bone growth or bone growth promotion, or any other surgical procedure or intervention affecting tissue in the oral cavity, anatomic structures in the oral cavity, or alveolar (jaw) bone. The need for applying the dental pad assembly 10 can also arise as a result of an accident that causes injury or trauma to tissue or structures in the oral cavity or alveolar (jaw) bone.

The site treated by the pad assembly 10 can involve arterial and/or venous bleeding caused by a surgical instrument or trauma or injury; or by the placement during surgery or a dental procedure of a wire, staples, fasteners, or sutures; or caused accidentally by a laceration, or a wound, or a puncture, or a burn, or a bone fracture, or crush injury. The dental pad assembly 10 can be sized and configured to be inserted or placed in association with any type of tissue disruption, trauma, or injury in the oral cavity or on or in proximity to adjacent anatomic structures.

Regardless of the cause, the properties of the matrix 12 of the pad assembly 10 serve to moderate bleeding, fluid seepage or weeping, or other forms of fluid loss, while also promoting healing.

Due to the properties of the matrix 12, the dental pad assembly 10 can also desirably form an anti-bacterial and/or anti-microbial and/or anti-viral protective barrier at or surrounding the tissue treatment site in an oral cavity.

Due to the special properties of the chitosan matrix 12, the dental pad assembly 10 also may be indicated for use with individuals undergoing dental procedures or suffering tissue trauma in the oral cavity, who have various types of bleeding or coagulation disorders, such as hemophilia, or idiopathic thrombocytopenic purpura (ITP) (which can itself lead to bleeding gums). The presence of the chitosan matrix 12 attracts red blood cell membranes, which fuse to chitosan matrix 12 upon contact. A clot can be formed very quickly and does not need the clotting proteins that are normally required for coagulation. Even in individuals without bleeding or coagulation disorders, the presence of the chitosan matrix 12 can accelerate the clotting process independent of the clotting cascade. For this reason, the matrix 12 can be used with no loss of efficacy in conjunction with anticoagulants/blood thinners such as heparin, clopidogrel (Plavix™), acetylsalicylic acid, dipyridamole, etc.

The dental pad assembly 10, when used during or after a dental procedure or accidental trauma in the oral cavity, can also provide a topically applied platform for the delivery of one or more therapeutic agents into the blood stream in a controlled release fashion. The therapeutic agents can be incorporated into the hydrophilic polymer sponge structure, e.g., either before or after the freezing step, and before the drying and densification steps, as will be described later. Examples of therapeutic agents that can be incorporated into a hydrophilic polymer sponge structure (e.g., the chitosan matrix 12) include, but are not limited to, drugs or medications, stem cells, antibodies, anti-microbials, anti-virals, collagens, genes, DNA, and other therapeutic agents; hemostatic agents like fibrin; growth factors; Bone Morphogenic Protein (BMP); and similar compounds.

The beneficial properties of chitosan matrix 12 includes adherence to mucosal surfaces within the body, such as those lining the mouth. This feature makes possible the incorporation of the chitosan matrix 12 in systems and devices directed to treating mucosal surfaces where the adhesive sealing characteristics, and/or accelerated clotting attributes, and/or anti-bacterial/anti-viral features of the chitosan matrix 12, as described, provide advantages. Such systems and methods can include the gum repairs and sealing about sutures placed in the oral cavity.

1. The Tissue Dressing Matrix

The tissue dressing matrix 12 is preferably formed from a low modulus hydrophilic polymer matrix, i.e., a inherently "uncompressed" tissue dressing matrix 12, which has been densified by a subsequent densification process, which will be described later. As previously described, the tissue dressing matrix 12 may comprise a hydrophilic polymer form, which, in a preferred form, comprises a non-mammalian material poly [β-(1→4)-2-amino-2-deoxy-D-glucopyranose, which is more commonly referred to as chitosan.

The chitosan selected for the matrix 12 preferably has a weight average molecular weight of at least about 100 kDa, and more preferably, of at least about 150 kDa. Most preferably, the chitosan has a weight average molecular weight of at least about 300 kDa.

In forming the matrix 12, the chitosan is desirably placed into solution with an acid, such as glutamic acid, lactic acid, formic acid, hydrochloric acid and/or acetic acid. Among these, hydrochloric acid and acetic acid are most preferred, because chitosan acetate salt and chitosan chloride salt resist dissolution in blood whereas chitosan lactate salt and chitosan glutamate salt do not. Larger molecular weight (Mw) anions disrupt the para-crystalline structure of the chitosan salt, causing a plasticization effect in the structure (enhanced flexibility). Undesirably, they also provide for rapid dissolution of these larger Mw anion salts in blood.

One preferred form of the matrix 12 comprises an "uncompressed" chitosan acetate matrix 12 of density less than 0.035 $g/cm^3$ that has been formed by freezing and lyophilizing a chitosan acetate solution, which is then densified by compression to a density of from 0.6 to 0.25 $g/cm^3$, with a most preferred density of about 0.20 $g/cm^3$. This chitosan matrix 12 can also be characterized as a compressed, hydrophilic sponge structure. The densified chitosan matrix 12 exhibits all of the above-described characteristics deemed to be desirable. It also possesses certain structural and mechanical benefits that lend robustness and longevity to the matrix during use, as will be described in greater detail later.

The chitosan matrix 12 presents a robust, permeable, high specific surface area, positively charged surface. The positively charged surface creates a highly reactive surface for red blood cell and platelet interaction. Red blood cell membranes are negatively charged, and they are attracted to the chitosan matrix 12. The cellular membranes fuse to chitosan matrix 12 upon contact. A clot can be formed very quickly, circumventing immediate need for clotting proteins that are normally required for hemostasis. For this reason, the chitosan matrix 12 is effective for both normal as well as anti-coagulated individuals, and as well as persons having a coagulation disorder like hemophilia. The chitosan matrix 12 also binds bacteria, endotoxins, and microbes, and can kill bacteria, microbes, and/or viral agents on contact.

Further details of the structure, composition, manufacture, and other technical features of the chitosan matrix 12 will be described later.

2. The Pouch

As FIGS. 5A and 5B show, the chitosan matrix 12—either in the form of a presized dental pad assembly 10 or as a larger source pad assembly 11 from which presized dental pad assemblies 10 can be cut—is desirably vacuum packaged before use with low moisture content, preferably 5% moisture or less, in an air-tight heat sealed foil-lined pouch 16. The dental pad assembly 10 or source assembly 11 is subsequently terminally sterilized within the pouch 16 by use of gamma irradiation. As FIG. 5B shows, a source pad assembly 11, from which smaller pad assemblies 10 can be cut and sized, can also be vacuum packaged in a sterile condition in a pouch 16 before use.

The pouch 16 is configured to be peeled opened by the caregiver at the instant of use. The pouch 16 provides peel away access to the tissue dressing pad assembly 10 along one end. The opposing edges of the pouch 16 are grasped and pulled apart to expose the tissue dressing pad assembly 10 for use.

3. Manipulating the Dental Pad Assembly

Figure 6:
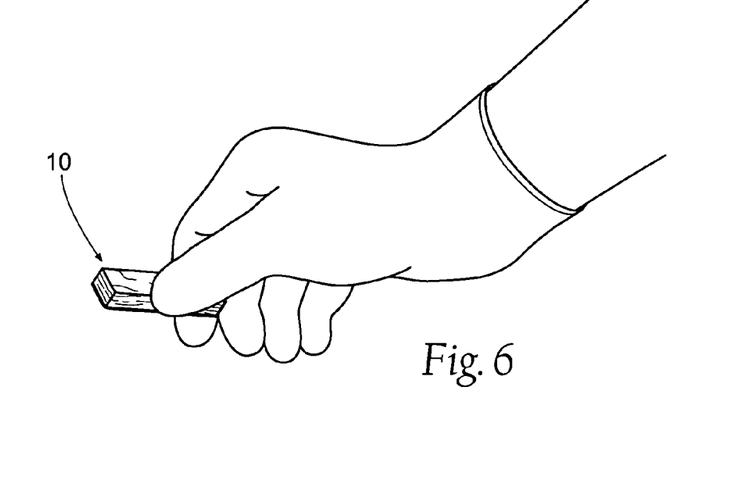
FIG. 6 is a perspective view of the dental pad assembly shown in FIG. 4A, after having been removed from the pouch shown in FIG. 5A in anticipation of use.

Once removed from the pouch 16 (see FIG. 6), the dental pad assembly 10 is immediately ready to be adhered to the targeted tissue site. It needs no pre-application manipulation to promote adherence. For example, there is no need to peel away a protective material to expose an adhesive surface for use. The adhesive surface forms in situ, because the chitosan matrix 12 itself exhibits strong adhesive properties once in contact with blood, fluid, or moisture. The dental pad assembly 10 need not be applied to the targeted site immediately upon opening the pouch 16.

Figure 7:
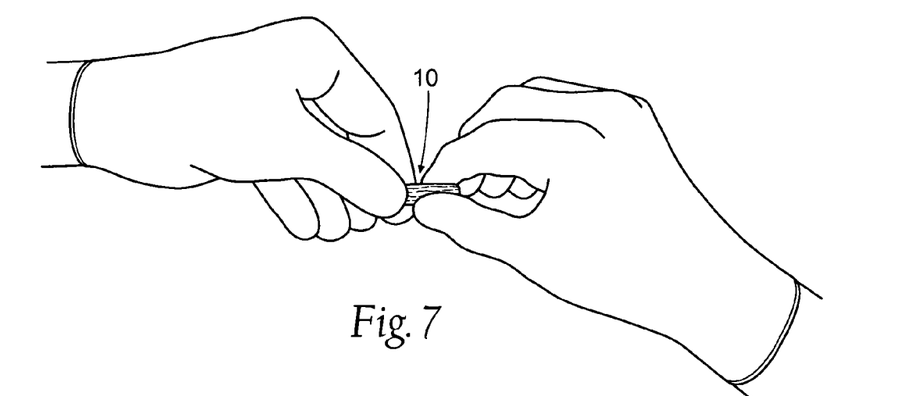
FIG. 7 is a perspective view of the dental pad assembly shown in FIG. 6 being held and manipulated by folding or bending prior to use to conform to the topology of a targeted tissue site.

As FIG. 7 shows, the dental pad assembly 10 can be shaped and adapted on site to conform to the topology and morphology of the targeted site, which in the illustrated embodiment is tooth socket following a tooth extraction. The practitioner can obtain a dental impression reflecting the size and spacing of teeth in the area of the extraction, and use the impression to aid in sizing and shaping the pad assembly 10. The dental pad assembly 10 can be deliberately molded into many configurations, e.g., into a cylinder or a cup-shape, to best conform to the particular topology and morphology of the treatment site. As previously described (see FIG. 4B), one or more pad assemblies 10 can be cut and shaped on site from a larger source assembly 11.

Figure 8:
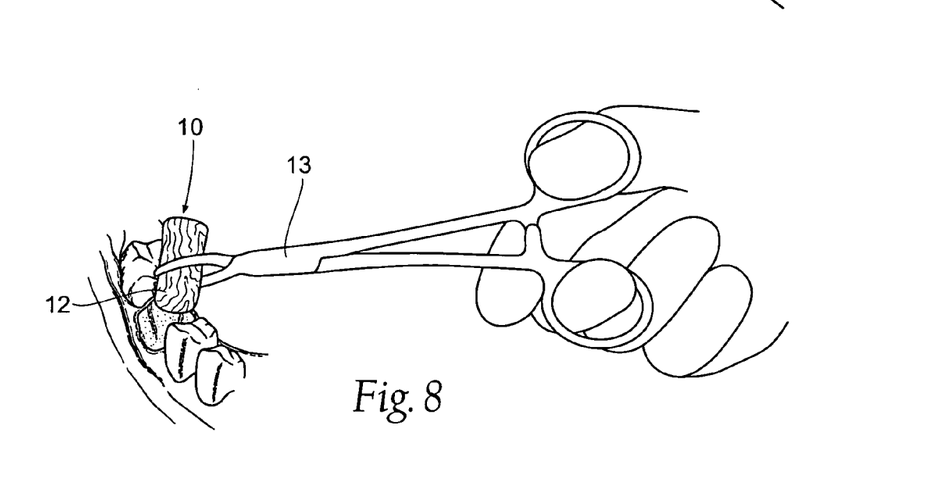
FIG. 8 is a perspective view of the dental pad assembly being placed within the targeted extraction site.
Figure 9:
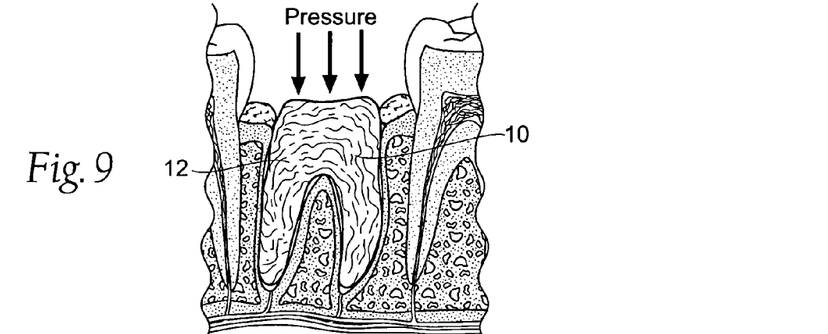
FIG. 9 is a side section view of the dental pad assembly, after placement within the targeted extraction site, with pressure being temporarily applied to adhere the pad assembly to the site and stanch bleeding.

FIG. 8 shows the chitosan dental pad assembly 10 being positioned in association with a targeted treatment site, which in the illustrated embodiment a tooth extraction site. As FIG. 8 shows, the dental pad assembly 10 is placed and pressed into the tooth socket (e.g., by hand or using a forceps 13) with the chitosan matrix 12 directed against the site of active bleeding or where adherence is otherwise desired, so that direct pressure can be applied to the bleeding tissue (see FIG. 9 also). Desirably, as FIG. 9 shows, the pad assembly 10 is shaped, sized, and configured so that a portion of the pad assembly 10 extends from the socket between the remaining teeth and is held in place by the opposing teeth. Desirably, once applied to a site where adherence is desired, the caregiver should avoid repositioning the dental pad assembly 10.

Desirably, as FIG. 9 shows, firm pressure is applied about two minutes, to allow the natural adhesive activity of the chitosan matrix 12 to develop. In this way, virtually all of the compressive force retained by the opposing teeth facing the extraction site is transmitted through substantially all of the mass of the pad assembly 10. The adhesive strength of the chitosan matrix 12 will increase with duration of applied pressure, up to about five minutes. Pressure applied evenly across the dental pad assembly 10 during this time (as shown by arrows in FIG. 9) will provide more uniform adhesion and wound sealing. Pressure can be applied with the aid of a gauze compress, if desired. The patient can also apply and maintain pressure by biting down.

The chitosan matrix 12 of the pad assembly 10 does more than soak up blood as a clot forms within the socket. The adhesive strength of the chitosan matrix 12 causes it to adhere to tissue within the socket, so that mechanical properties of the pad assembly 10 apply direct pressure. Further, the presence of the chitosan matrix 12 attracts red blood cell membranes, which fuse to chitosan matrix 12 upon contact. A clot can be formed very quickly and does not depend solely upon the clotting proteins that are normally required for coagulation. The presence of the chitosan matrix 12 can accelerate the clotting process independent of the clotting cascade. Also further, the presence of the chitosan matrix 12 can provide an anti-bacterial and/or anti-microbial and/or anti-viral protective effect. Hemostasis occurs in about one minute using the chitosan matrix 12 in dental applications, compared to about seven minutes using conventional cotton packs and rolled or folded gauze pads.

The dental pad assembly 10 can be torn or cut on site to match the size of the extraction site, as previously described. Smaller, patch pieces of a pad assembly 10 can also be cut to size on site, and fitted and adhered in other pieces already placed to best approximate the topology and morphology of the treatment site.

Desirably, the dental pad assembly 10 is allowed to reside within the socket during the healing process for the prevention of pain and the promotion of rapid healing. The presence of chitosan matrix 12 within the socket provides an environment conducive to retention of the clot (thereby avoiding dry socket) as well as the general healing process, during which new bone and gum tissue grow into the gap left by the extraction. The physical presence of the chitosan matrix 12—which, desirably, is purposely densified during its manufacture to resist dissolution—acts as a bone covering obtundant and physiologic scaffolding for the conduction of normal alveolar bone heal process of fibroblast ingrowth, blood vessel formation, and reossification of the extraction site. The enhanced physical properties of the densified chitosan matrix 12 further enhanced by the adhesive strength of the chitosan matrix 12, its self-promotion of coagulation, and its anti-bacterial/anti-microbia/anti-viral properties.

As previously described, the pad assembly 10 can incorporate a medication or physiologic or pharmacologic agent that acts locally or systemically in the body, e.g., enzymes, organic catalysts, ribozymes, organometallics, proteins, glycoproteins, peptides, polyamino acids, antibodies, nucleic acids, steroidal molecules, antibiotics, antimycotics, cytokines, growth factors for tissue and/or bone, carbohydrates, oleophobics, lipids, extracellular matrix and/or individual components, mammalian cells, stem cells, genetically engineered cells, pharmaceuticals, and thereapeutics. The pad assembly 10 provides a physically stable, biocompatible, and non-cytotoxic environment promoting a rapid and pain-free recovery period.

Desirably, the pad assembly 10 is removed and, if indicated, replaced within forty-eight hours of application. The pad assembly 10 can be peeled away and will generally separate from the treatment site in a single, intact dressing. In some cases, residual chitosan gel may remain, and this can be removed using a saline or water wash, with gentle abrasion using a gauze dressing, if required.

Chitosan is biodegradable within the body and is broken down into glucosamine, a benign substance. Still, efforts should be made to remove all portions of chitosan from the wound at the time of definitive repair.

II. Manufacture of the Dental Pad Assembly

A desirable methodology for making the tissue dressing pad assembly 10 will now be described. This methodology is shown schematically in FIG. 10, A to H. It should be realized, of course, that other methodologies can be used.

1. Preparation of a Chitosan Solution

The chitosan used to prepare the chitosan solution (designated CS in FIG. 10, Step A) preferably has a fractional degree of deacetylation greater than 0.78 but less than 0.97. Most preferably the chitosan has a fractional degree of deacetylation greater than 0.85 but less than 0.95. Preferably the chitosan selected for processing into the matrix has a viscosity at 25° C. in a 1% (w/w) solution of 1% (w/w) acetic acid (AA) with spindle LVI at 30 rpm, which is about 100 centipoise to about 2000 centipoise. More preferably, the chitosan has viscosity at 25° C. in a 1% (w/w) solution of 1% (w/w) acetic acid (AA) with spindle LVI at 30 rpm, which is about 125 centipoise to about 1000 centipoise. Most preferably, the chitosan has viscosity at 25° C. in a 1% (w/w) solution of 1% (w/w) acetic acid (AA) with spindle LV1 at 30 rpm, which is about 400 centipoise to about 800 centipoise.

Figure 10:
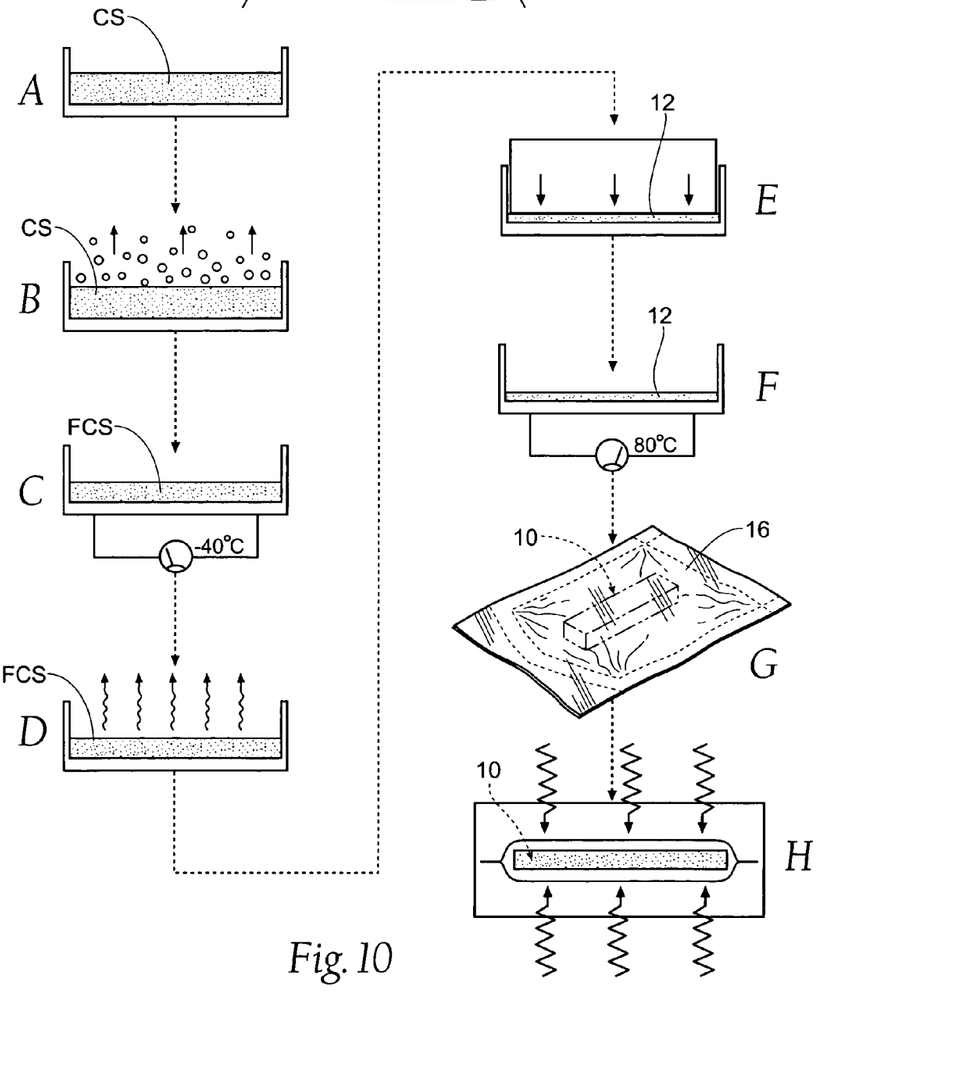
FIG. 10 is a diagrammatic view of the steps of a representative process for creating the dental pad assembly shown in FIG. 6.

The chitosan solution CS is preferably prepared at 25° C. by addition of water to solid chitosan flake or powder and the solid dispersed in the liquid by agitation, stirring or shaking (see FIG. 10, Step A). On dispersion of the chitosan in the liquid, the acid component is added and mixed through the dispersion to cause dissolution of the chitosan solid. The rate of dissolution will depend on the temperature of the solution, the molecular weight of the chitosan and the level of agitation. Preferably the dissolution step is performed within a closed tank reactor with agitating blades or a closed rotating vessel. This ensures homogeneous dissolution of the chitosan and no opportunity for high viscosity residue to be trapped on the side of the vessel. Preferably the chitosan solution percentage (w/w) is greater than 0.5% chitosan and less than 2.7% chitosan. More preferably the chitosan solution percentage (w/w) is greater than 1% chitosan and less than 2.3% chitosan. Most preferably the chitosan solution percentage is greater than 1.5% chitosan and less than 2.1% chitosan. Preferably the acid used is acetic acid. Preferably the acetic acid is added to the solution to provide for an acetic acid solution percentage (w/w) at more than 0.8% and less than 4%. More preferably the acetic acid is added to the solution to provide for an acetic acid solution percentage (w/w) at more than 1.5% (w/w) and less than 2.5%.

The structure or form producing steps for the chitosan matrix 12 are typically carried out from solution and can he accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. In the case of freezing, where two or more distinct phases are formed by freezing (typically water freezing into ice with differentiation of the chitosan biomaterial into a separate solid phase), another step is required to remove the frozen solvent (typically ice), and hence produce the chitosan matrix 12 without disturbing the frozen structure. This may be accomplished by a freeze-drying and/or a freeze substitution step. The filament can he formed into a non-woven sponge-like mesh by non-woven spinning processes. Alternately, the filament may he produced into a felted weave by conventional spinning and weaving processes. Other processes that may be used to make the biomaterial sponge-like product include dissolution of added porogens from a solid chitosan matrix 12 or boring of material from said matrix.

2. Degassing the Aqueous Chitosan Solution

Preferably (see FIG. 10, Step B), the chitosan biomaterial solution CS is degassed of general atmospheric gases. Typically, degassing is removing sufficient residual gas from the chitosan biomaterial solution CS so that, on undergoing a subsequent freezing operation, the gas does not escape and form unwanted large voids or large trapped gas bubbles in the subject wound dressing product. The degassing step may be performed by heating a chitosan biomaterial, typically in the form of a solution CS, and then applying a vacuum thereto. For example, degassing can be performed by heating a chitosan solution to about 45° C. immediately prior to applying vacuum at about 500 mTorr for about 5 minutes while agitating the solution.

In one embodiment, certain gases can be added back into the solution to controlled partial pressures after initial degassing. Such gases would include but are not limited to argon, nitrogen and helium. An advantage of this step is that solutions containing partial pressures of these gases form microvoids on freezing. The microvoid is then carried through the sponge as the ice-front advances. This leaves a well defined and controlled channel that aids sponge pore interconnectivity.

3. Freezing the Aqueous Chitosan Solution

Next (see FIG. 10, Step C), the chitosan biomaterial—which is typically now in acid solution and degassed, as described above—is subjected to a freezing step. Freezing is preferably carried out by cooling the chitosan biomaterial solution supported within a mold and lowering the solution temperature from room temperature to a final temperature below the freezing point. More preferably this freezing step is performed on a plate freezer whereby a thermal gradient is introduced through the chitosan solution in the mold by loss of heat through the plate cooling surface. Preferably this plate cooling surface is in good thermal contact with the mold. Preferably the temperature of the chitosan solution and mold before contact with the plate freezer surface are near room temperature. Preferably the plate freezer surface temperature is not more than −10° C. before introduction of the mold+solution. Preferably the thermal mass of the mold+solution is less than the thermal mass of the plate freezer shelf+heat transfer fluid. Preferably the molds are formed from, but are not limited to, a metallic element such as iron, nickel, silver, copper, aluminum, aluminum alloy, titanium, titanium alloy, vanadium, molybdenum, gold, rhodium, palladium, platinum and/or combinations thereof. The molds may also be coated with thin, inert metallic coatings such as titanium, chromium, tungsten, vanadium, nickel, molybdenum, gold and platinum in order to ensure there is no reaction with the acid component of the chitosan solution and the chitosan salt matrix. Thermally insulating coatings or elements may be used in conjunction with the metallic molds to control heat transfer in the molds. Preferably the mold surfaces do not bind with the frozen chitosan solution. The inside surface of the mold is preferably coated with a thin, permanently-bound, fluorinated release coating formed from polytetrafluoroethylene (Teflon), fluorinated ethylene polymer (FEP), or other fluorinated polymeric materials. Although coated metallic molds are preferable, thin walled plastic molds can be a convenient alternative for supporting the solution. Such plastic molds would include, but not be limited to, molds prepared by injection molding, machining or thermoforming from polyvinylchloride, polystyrene, acrylonitrile-butadiene-styrene copolymers, polyesters, polyamides, polyurethanes and polyolefins. An advantage of the metallic molds combined with local placement of thermally insulating elements is that they also provide opportunity for improved control of heat flow and structure within the freezing sponge. This improvement in heat flow control results from large thermal conductivity differences between thermally conducting and thermally insulating element placements in the mold.

Freezing of the chitosan solution in this way (forming a frozen chitosan solution, designed FCS in FIG. 10, Step C) enables the preferred structure of the pad assembly product to be prepared.

The plate freezing temperature affects the structure and mechanical properties of the final chitosan matrix 12. The plate freezing temperature is preferably not higher than about −10° C., more preferably not more than about −20° C., and most preferably not more than about −30° C. When frozen at −10° C., the structure of the uncompressed chitosan matrix 12 is very open and vertical throughout the open sponge structure. When frozen at −25° C., the structure of the uncompressed chitosan matrix 12 is more closed, but it is still vertical. When frozen at −40° C., the structure of the uncompressed chitosan matrix 12 is closed and not vertical. Instead, the chitosan matrix 12 comprises more of a reinforced, intermeshed structure. The adhesive/cohesive sealing properties of the chitosan matrix 12 are observed to improve as lower freezing temperatures are used. A freezing temperatures of about −40° C. forms a structure for the chitosan matrix 12 having superior adhesive/cohesive properties.

During the freezing step, the temperature may be lowered over a predetermined time period. For example, the freezing temperature of a chitosan biomaterial solution may be lowered from room temperature to −45° C. by plate cooling application of a constant temperature cooling ramp of between about −0.4° C./mm to about −0.8° C./mm for a period of about 90 minutes to about 160 minutes.

4. Freeze Drying the Chitosan/Ice Matrix

The frozen chitosan/ice matrix (FCS) desirably undergoes water removal from within the interstices of the frozen material (see FIG. 10, Step D). This water removal step may be achieved without damaging the structural integrity of the frozen chitosan biomaterial FCS. This may be achieved without producing a liquid phase, which can disrupt the structural arrangement of the ultimate chitosan matrix 12. Thus, the ice in the frozen chitosan biomaterial FSC passes from a solid frozen phase into a gas phase (sublimation) without the formation of an intermediate liquid phase. The sublimated gas is trapped as ice in an evacuated condenser chamber at substantially lower temperature than the frozen chitosan biomaterial.

The preferred manner of implementing the water removal step is by freeze-drying, or lyophilization. Freeze-drying of the frozen chitosan biomaterial FCS can be conducted by further cooling the frozen chitosan biomaterial. Typically, a vacuum is then applied. Next, the evacuated frozen chitosan material may be gradually heated.

More specifically, the frozen chitosan biomaterial may be subjected to subsequent freezing preferably at about −15° C., more preferably at about −25° C., and most preferably at about −45° C., for a preferred time period of at least about 1 hour, more preferably at least about 2 hour, and most preferably at least about 3 hour. This step can be followed by cooling of the condenser to a temperature of less than about −45° C., more preferably at about −60° C., and most preferably at about −85° C. Next, a vacuum in the amount of preferably at most about 100 mTorr, more preferably at most about 150 mTorr, and most preferably at least about 200 mTorr, can be applied. The evacuated frozen chitosan material can be heated preferably at about −25° C., more preferably at about −15° C., and most preferably at about −10° C., for a preferred time period of at least about 1 hour, more preferably at least about 5 hour, and most preferably at least about 10 hour.

Further freeze drying, maintaining vacuum pressure at near 200 mTorr, is conducted at a shelf temperature of about 20° C., more preferably at about 15° C., and most preferably at about 10° C., for a preferred time period of at least about 36 hours, more preferably at least about 42 hours, and most preferably at least about 48 hours.

5. Densification of the Chitosan Matrix

The chitosan matrix before densification (density near 0.03 g/cm$^3$) will be called an "uncompressed chitosan matrix." This uncompressed matrix is not ideal in stanching bleeding, since it may rapidly dissolve in blood and possess poor mechanical properties. The chitosan biomaterial is therefore desirably compressed (see FIG. 10, Step E). Compression loading normal to the hydrophilic matrix polymer surface with heated platens can be used to compress the dry "uncompressed" chitosan matrix 12 to reduce the thickness and increase the density of the matrix. The compression step, which will sometimes be called in shorthand "densification," significantly increases adhesion strength, cohesion strength and dissolution resistance of the chitosan matrix 12. Appropriately frozen chitosan matrices 12 compressed above a threshold density (close to 0.1 g/cm³) do not readily dissolve in flowing blood at 37° C.

The compression temperature is preferably not less than about 60° C., more preferably it is not less than about 75° C. and not more than about 85° C.

After densification, the density of the matrix 12 can be different at the base ("active") surface of the matrix 12 (i.e., the surface exposed to tissue) than at the top surface of the matrix 12. For example, in a typical matrix 12 where the mean density measured at the active surface is at or near the most preferred density value of 0.2 g/cm³, the mean density measured at the top surface can be significantly lower, e.g., at 0.05 g/cm³. The desired density ranges as described herein for a densified matrix 12, are intended to exist at are near the active side of the matrix 12, where exposure to blood, fluid, or moisture first occurs.

The densified chitosan biomaterial is next preferably preconditioned by heating chitosan matrix 12 in an oven to a temperature of preferably up to about 75° C., more preferably to a temperature of up to about 80° C., and most preferably to a temperature of preferably up to about 85° C. (FIG. 16, Step F). Preconditioning is typically conducted for a period of time up to about 0.25 hours, preferably up to about 0.35 hours, more preferably up to about 0.45 hours, and most preferably up to about 0.50 hours. This pre-conditioning step provides further significant improvement in dissolution resistance with a small cost in a 20-30% loss of adhesion properties.

6. Placement in the Pouch

The tissue dressing pad assembly 10 can he subsequently packaged in the pouch 16 (see FIG. 16, Step F), either in a precut size or as a source pad assembly 11. The pouch 16 is desirably purged with an inert gas such as either argon or nitrogen gas, evacuated and heat sealed. The pouch 16 acts to maintain interior contents sterility over an extend time (at least 24 months) and also provides a very high barrier to moisture and atmospheric gas infiltration over the same period.

7. Sterilization

After pouching, the processed tissue dressing pad assembly 10 is desirably subjected to a sterilization step (see FIG. 10, Step G). The tissue dressing pad assembly 10 can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy.

8. Improving Compliance and Flexibility

Bending and/or molding of the pad assembly 10 prior to placement on the targeted treatment of injury site has been already described and recommended. In hydrophilic polymer sponge structures, of which the pad assembly 10 is but one example, the more flexible and compliant the structure is, the more resistant it is to tearing and fragmentation as the structure is made to conform to the shape of the targeted treatment site and achieve apposition of the sponge structure with the underlying (typically) irregular surface of the injury. Resistance to tearing and fragmentation is a benefit, as it maintains wound sealing and hemostatic efficacy.

Improved compliance and flexibility can be achieved by mechanical manipulation of any hydrophilic polymer sponge structure during or after manufacture, without loss of beneficial features of robustness and longevity of resistance to dissolution.

There are several ways in which such mechanical manipulation can be accomplished during or after manufacture; for example, (i) by controlled micro-fracturing of the substructure of a hydrophilic polymer sponge structure by rolling, bending, twisting, rotating, vibrating, probing, compressing, extending, shaking and kneading; (ii) controlled macro-texturing (by the formation of deep relief patterns) in a given hydrophilic polymer sponge structure by thermal compression techniques at 80° C.; and (iii) by controlled formation of vertical channels into a given hydrophilic polymer sponge structure during the freezing step of the sponge structure preparation, or alternatively it may be achieved mechanically by perforation of the sponge structure during the compression (densification) step.

Further details of mechanical manipulations that can be performed to improve compliance and flexibility are shown in co-pending U.S. patent application Ser. No. 11/020,365, filed Dec. 23, 2004, and entitled "Tissue Dressing Assemblies, Systems, and Methods Formed From Hydrophilic Polymer Sponge Structures Such as Chitosan," which is incorporated herein by reference.

III. Alternative Embodiments

The dental pad assembly 10 can be provided in various alternative forms.

Figure 11A:
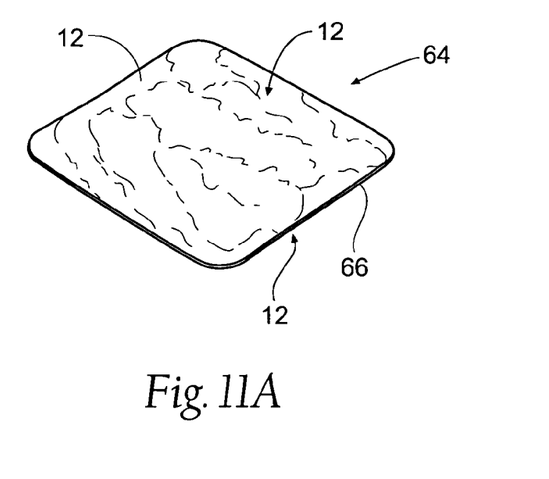
FIGS. 11A and 11B are, respectively, a perspective assembled view and a perspective exploded view of an alternative embodiment of a dental pad assembly for treating tissue or bone in an oral cavity or an adjacent anatomic structure, comprising a hydrophilic polymer sponge structure incorporated into a tissue dressing sheet assembly.
Figure 11B:
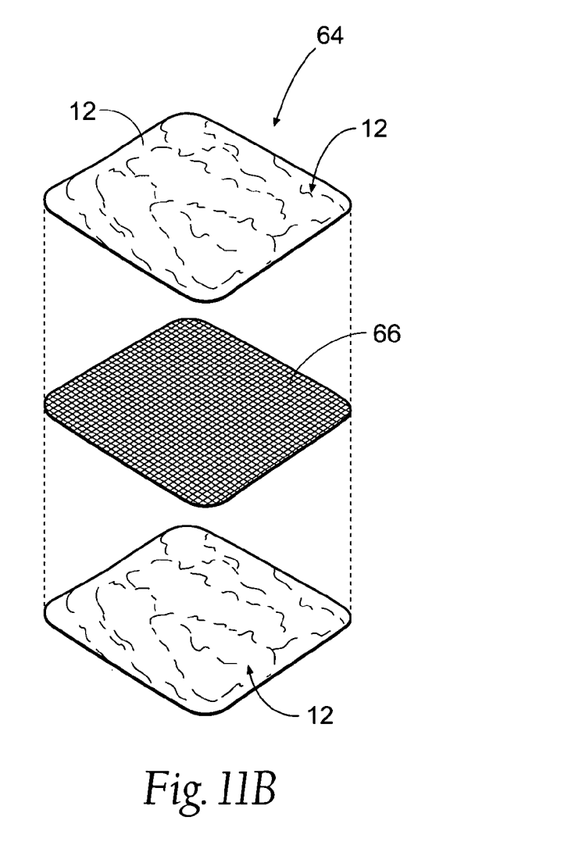
Figure 11C:
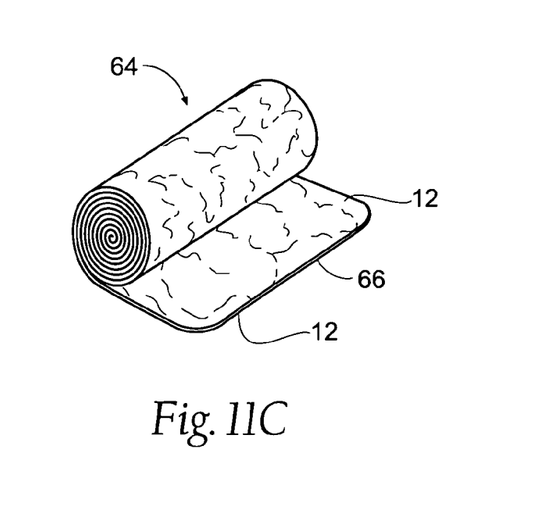
FIG. 11C is a perspective view of the tissue dressing sheet assembly being shaped and configured into a roll form for placement into contact with tissue or bone in an oral cavity or an adjacent anatomic structure.

For example, as shown in FIGS. 11A and 11B, a pad assembly 64 can comprise a sheet 66 of woven or non-woven mesh material enveloped between layers of the tissue dressing matrix 12. The tissue dressing matrix 12 impregnates the sheet 66. The size, shape, and configuration of the tissue dressing sheet assembly 64 can vary according to its intended use. The sheet pad assembly 64 can be rectilinear, elongated, square, round, oval, or composite or complex combinations thereof. The tissue dressing sheet assembly 64 is preferably thin (compared to the pad assembly 10), being in the range of between 0.5 mm to 1.5 mm in thickness. A preferred form of the thin reinforced structure of the sheet assembly 64 comprises a chitosan matrix 12 or sponge, at the typical chitosan matrix density of 0.10 to 0.20 g/cm3, reinforced by absorbable bandage webbing such as cotton gauze and the resultant bandage thickness is 1.5 mm or less. The sheet 66 can comprise woven and non-woven mesh materials, formed, e.g., from cellulose derived material such as gauze cotton mesh. The sheet assembly 64 accommodates layering, compaction, and/or rolling—i.e., "stuffing" (as FIG. 11C shows)—of the hydrophilic polymer sponge structure (e.g., the chitosan matrix 12) within a wound site using pressure to further reinforce the overall structure against arterial and venous bleeding. By stuffing of the sheet structure over itself, as FIG. 11C shows, the interaction of the blood with the hydrophilic polymer (e.g., chitosan) infused within the webbing provides for a highly adhesive, insoluble and highly conforming packing form.

Further details of the sheet assembly 64 can be founding in co-pending U.S. patent application Ser. No. 11/020,365, filed Dec. 23, 2004, and entitled "Tissue Dressing Assemblies, Systems, and Methods Formed From Hydrophilic Polymer Sponge Structures Such as Chitosan," which is incorporated herein by reference.

IV. CONCLUSION

It has been demonstrated that a hydrophilic polymer sponge structure like the chitosan matrix 12 can be readily adapted for association with dressings or platforms of various sizes and configurations in association with dental procedures or trauma involving the oral cavity—in pad form, in sheet form, or in otherwise compliant form.

Therefore, it should be apparent that above-described embodiments of this invention are merely descriptive of its principles and are not to be limited. The scope of this invention instead shall be determined from the scope of the following claims, including their equivalents.

We claim:

1. A method comprising:
providing a hydrophilic polymer sponge structure comprising a chitosan biomaterial, wherein said chitosan biomaterial has been freeze-dried and heat compressed to form said hydrophilic sponge structure;
placing said hydrophilic polymer sponge structure in association with tissue or bone in an oral cavity or an anatomic structure adjacent to said oral cavity;
applying pressure to said polymer sponge structure to thereby adhere said polymer sponge structure to said tissue or bone.

2. A method according to claim 1 wherein the hydrophilic polymer sponge structure has been densified by compression prior to use to a density of between 0.6 to 0.1 g/cm$^3$.

3. A method according to claim 1 wherein hydrophilic polymer sponge structure is placed within a tooth extraction socket.

4. A method comprising:
providing a hydrophilic polymer sponge structure comprising a chitosan biomaterial, wherein said chitosan biomaterial has been freeze-dried and heat compressed to form said hydrophilic sponge structure;
performing a surgical procedure including at least one of a tooth extraction, or endodontic surgery, or periodontal surgery, or orthodontic treatment, or orthognathic surgery, or biopsy, or gingival surgery, osseous surgery, scaling or root planning, periodontal maintenance, complete maxillary or mandibular denture, or complete or partial denture adjustment, or denture rebase or reline, or soft tissue surgical extraction, or bony surgical extraction, or installation of an occlusal orthotic device or occlusal guard or occlusal adjustment, or oral surgery involving jaw repair, or bone growth or bone growth promotion, or any other surgical procedure or intervention affecting tissue in the oral cavity, anatomic structures in the oral cavity, or alveolar (jaw) bone;
shaping said hydrophilic polymer structure prior to placement in connection with said surgical procedure;
placing said hydrophilic polymer sponge structure in association with tissue or bone affected by the surgical procedure; and
applying pressure to said polymer sponge structure to thereby adhere said polymer sponge structure to said tissue or bone affected by the surgical procedure.

5. A method comprising
providing a hydrophilic polymer sponge structure comprising a chitosan biomaterial, wherein said chitosan biomaterial has been freeze-dried and heat compressed to form said hydrophilic sponge structure;
treating tissue in the oral cavity or alveolar (jaw) bone as a result of an accident that causes injury or trauma to the tissue or bone,
placing said hydrophilic polymer sponge structure in association with the treated tissue or bone; and
forming a clot with said hydrophilic sponge structure in conjunction with the treated tissue or bone, thereby promoting hemostasis for the treated tissue.

6. A method according to claim 4 or 5 wherein the hydrophilic polymer sponge structure has been densified by compression prior to use to a density of between 0.6 to 0.1 g/cm$^3$.

* * * * *